United States Patent
Ikeda (10) Patent No.: US 7,241,378 B2
(45) Date of Patent: Jul. 10, 2007

(54) HEMODIALYSIS APPARATUS

(75) Inventor: Atsushi Ikeda, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 114 days.

(21) Appl. No.: 10/484,850

(22) PCT Filed: Jul. 26, 2002

(86) PCT No.: PCT/JP02/07597

§ 371 (c)(1),
(2), (4) Date: Apr. 12, 2004

(87) PCT Pub. No.: WO03/009888

PCT Pub. Date: Feb. 6, 2003

(65) Prior Publication Data

US 2004/0238418 A1 Dec. 2, 2004

(30) Foreign Application Priority Data

Jul. 27, 2001 (JP) ............................ 2001-228628
Jul. 26, 2002 (JP) ............................ 2002-217467

(51) Int. Cl.
*B01D 61/32* (2006.01)
(52) U.S. Cl. ..................... 210/143; 210/86; 210/97; 210/321.65; 210/646; 210/739; 210/744
(58) Field of Classification Search .................. 210/86, 210/97, 321.65, 646, 739, 744, 143
See application file for complete search history.

(56) References Cited

U.S. PATENT DOCUMENTS 4,469,593 A * 9/1984 Ishihara et al. ............ 210/96.2
5,416,027 A * 5/1995 Baudin et al. ................ 436/70
6,602,424 B1 * 8/2003 Kramer et al. .............. 210/739

FOREIGN PATENT DOCUMENTS

| JP | 5-76445 U | 10/1993 |
| JP | 11-221275 A | 8/1999 |
| JP | 2002-186666 A | 7/2002 |

OTHER PUBLICATIONS

English translation copy of Japanese Patent No. 11-221275.*

* cited by examiner

*Primary Examiner*—John Kim
(74) *Attorney, Agent, or Firm*—Foley and Lardner LLP (57) ABSTRACT

A hemodialysis apparatus includes means for measuring or calculating a blood volume or a blood volume change as a blood index level, a hemodialysis means, and a controlling means that controls hemodialysis conditions of the hemodialysis means according to the blood index level. The controlling means controls the hemodialysis means so that hemodialysis operation is carried out without performing water removal at the time of the initiation of the hemodialysis operation until the blood volume stabilizes. The hemodialysis operation is carried out by performing water removal after the blood volume is stabilized by the hemodialysis operation without performing water removal, and that is a constitution so that it is possible to calculate the primary blood volume ($BV_0$) of each patient according to the following formula (I), from % $\Delta BV$ of hemodialysis operation which has been carried out before the blood volume is stabilized, and the increased blood volume circulating outside the body. The primary blood volume ($BV_0$) =increased blood volume circulating outside the body (space outside the body)/% $\Delta BV_x$. (I), wherein % $\Delta BV_x$ is the ratio of the volume change of the blood volume (BV) when hemodialysis is performed without performing water removal.

2 Claims, 3 Drawing Sheets

HEMODIALYSIS APPARATUS

TECHNICAL FIELD

The present invention relates to a blood treatment apparatus, especially to a hemodialysis apparatus which can control water removal conditions and water removal speed so as to prevent excessive water removal and also lack of water removal in the contrary, which occur frequently during hemodialysis.

BACKGROUND ART

For treating patients with impaired kidney function, treatments by purifying blood by dialysis or filtration via semipermeable membrane have been provided conventionally. As for this apparatus, it is important to appropriately maintain the blood volume circulating in the patient body, to perform safe and effective blood purification. A rapid or excessive water removal will decrease excessively patient's blood circulating volume, and it may cause reduction of blood pressure, shock or the like. On the contrary, if the water removal is slow, it will take a long time for blood purification, and if sufficient water removal cannot be made, there is a fear that hypertension, heart failure or the like can occur. Therefore, a hemodialysis apparatus performing water removal by monitoring patient's blood condition has been developed. For example, in Japanese Laid-Open Patent Publication No. 6-83723, an estimating apparatus which estimates the body fluid condition with a Hematocrit meter, and a controlling apparatus which controls the blood pump or ultra pressure by the output of said estimating apparatus are described. Concerning this apparatus, it is convenient as the water removal is controlled directly according to the measured body fluid condition, but on the other hand, as the water removal is controlled directly by the measured value, in case the result of the measuring means is not accurate or a trouble happens, it may cause a significant problem. Therefore, in such feed-forward control, generally, a separate line independent from the control line is disposed and a safety mechanism is loaded on said line. However, the apparatus becomes complicated when an independent line or safety mechanism is disposed and the operation becomes difficult. Furthermore, the cost of the apparatus will rise. Therefore, a simple apparatus as described in Japanese Laid-Open Patent Application No. 9-149935 was also developed. In other words, while monitoring the patient's blood condition, an alarm is ringed depending to the condition, and the water removal pump is stopped. However, this apparatus only recognizes if the water removal control is performed under the same control condition at the time of the initiation of dialysis, by comparing with the blood concentration measured before the initiation of dialysis, and it is not possible to perform adequate water removal to each patent. Furthermore, if the water removal is not performed according to the condition, the operator has to adjust each time the water removal volume or fluid replacement volume. Thus, even though it was safe, it was complicated and the human cost was high. Moreover, as for said apparatus, a means for measuring the blood condition is disposed on the line at the vein fluid side of the blood cycle, the blood condition after having passed the blood treatment machine (dialyser) is measured, thus it may not reflect the patient's direct blood condition.

To provide a blood treatment apparatus which have solved the problems mentioned above, that is, to provide a convenient apparatus at a low cost by making a structure wherein each patient's blood condition is monitored, enabling to perform blood treatment adequate to each patient chronologically, by not imposing much burden to the operator during its use, and by making the construction of the blood treatment apparatus simple, the present inventors provided a blood treatment apparatus (Japanese Laid-Open Patent Application No. 11-22175), comprising a blood measuring means for measuring blood parameters; a working unit for performing blood treatment; and a controlling unit controlling the working unit to perform blood treatment under prescribed blood treatment condition, wherein the controlling unit indicates the change of the blood treatment condition to the working unit, by setting a blood indication region determined beforehand against the patient blood indication level obtained with said blood measuring means, according to the chronological transition of said blood indication level in said blood indication region. Furthermore, the present inventors have improved said blood treatment apparatus (Japanese Laid-Open Patent Application No. 11-22175), and proposed a blood treatment apparatus (Japanese Laid-Open Patent Application No. 2001-540), wherein by monitoring each patient's blood condition, the condition of hemodialysis adequate to each patient chronologically, especially the water removal speed can be easily changed and defined. Said blood treatment apparatus (Japanese Laid-Open Patent Application No. 2001-540) is a hemodialysis apparatus comprising at least:(A) a blood measuring means for measuring blood parameter, (B) a working unit for performing blood treatment; and (C) a controlling unit for controlling the working unit to perform blood treatment under prescribed blood treatment condition; wherein the hemodialysis apparatus has a mechanism for controlling the water removal speed, and the controlling unit (C) incorporates the blood indicating level obtained from the patients' samples by the blood measuring means (A), monitoring if it transits or not within the defined range defined beforehand of blood indication level (hereinafter also referred to as defined range of blood indication level), and when said blood indication level being the target to control deviates from said range defined beforehand, the water removal speed of the working unit (B) can be changed at a speed rate defined beforehand.

As for the hemodialysis apparatus mentioned above, it was possible to manage surely the blood indication level at each point during hemodialysis treatment, but because it was necessary to define the region of the target blood indication level at each point, the operation was complicated. Furthermore, as the defined blood indication level was designated as a range, as long as a blood indication level exists within the defined range, even it is at the absolute edge of the range, the control mechanism of the hemodialysis apparatus would not work. Therefore, in case the blood indication level actually measured is slightly missing the point from the target, there was a fear that the control would be delayed. Furthermore, as for said apparatus, minute details were defined in each region, and the control is carried out according to these, the physiological water removal adequate to each patient was difficult to be carried out. On the contrary, when the water removal mild to the living body is intended to be carried out, it happened that the water removal volume which was determined beforehand, can not be attained.

DISCLOSURE OF THE INVENTION

The object of the present invention is to provide a hemodialysis apparatus that can achieve the following effects:

(1) The control mechanism is simple, and there is little risk of misoperation or out-of-control.
(2) As there is no need of difficult installation or unnecessary operation, the operator can easily operate without difficulty.
(3) As the control is carried out rapidly and finely, the blood volume can be transited fairly during the hemodialysis.

The present invention provides a hemodialysis apparatus having a means for measuring or calculating a blood volume or a blood volume change as a blood index level, a hemodialysis means, and a controlling means that controls hemodialysis conditions of the hemodialysis means according to the blood index level, wherein the controlling means controls the hemodialysis means to perform hemodialysis operation without performing water removal until the blood volume stabilizes, at the initiation of hemodialysis operation, and then to perform hemodialysis operation by performing water removal after the blood volume is stabilized by the hemodialysis operation without water removal, and which is constituted so that it is possible to calculate the primary blood volume of each patient ($BV_0$) according to the following formula (I) or (II).

1. Calculation of the primary blood volume ($BV_0$) according to formula (I)

Figure 3:
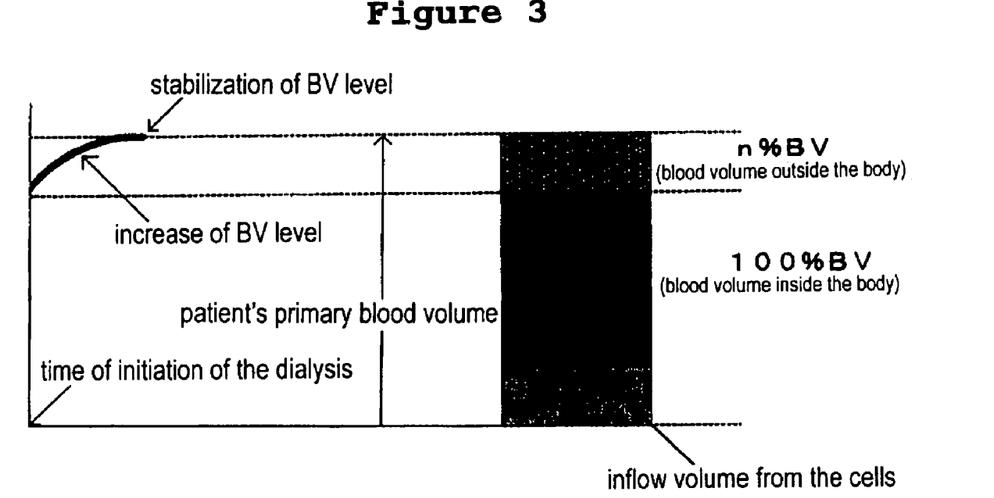
FIG. 3 is a figure explaining the first calculating method of the primary blood volume (BVo).

The first calculation method of the primary blood volume (BV0) is explained according to FIG. 3.

At the time of the initiation of hemodialysis, as the blood volume is not stable, when performing hemodialysis without performing water removal the turgor pressure inside the cells is sufficiently high, and the water runs over from cells to intercellular substances, it is believed that water corresponding to the increased blood circulating space of the hemodialysis apparatus will move from the cells to the blood vessel. Therefore, it is possible to obtain the primary blood volume ($BV_0$) of each patient, according to the following formula (I) with the increased blood circulating space of the hemodialysis apparatus and % $\Delta BV_x$. Primary blood volume ($BV_0$)=increased blood circulating space of the hemodialysis apparatus /% $\Delta BV_x$ . . . (I) [wherein % $\Delta BV_x$ is the ratio of the volume change of the blood volume (BV) when hemodialysis is performed without performing water removal]

(2) Calculation of the primary blood volume ($BV_0$) according to (II)

Figure 4:
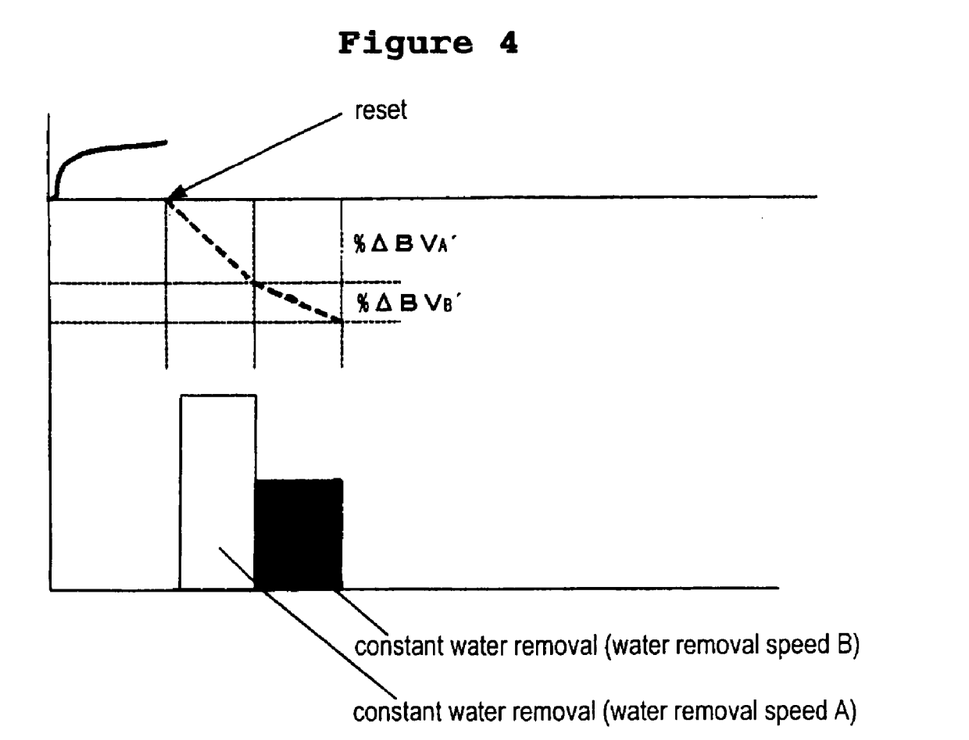
FIG. 4 is a figure explaining the second calculating method of the primary blood volume (BVo).

The second calculation method of the primary blood volume (BV0) is explained according to FIG. 4.

At the time of the initiation of hemodialysis, hemodialysis is performed without water removal until the blood volume stabilizes, and when the blood volume (BV) level becomes stable, hemodialysis accompanied by water removal is initiated, and at the same time as said hemodialysis is initiated, the water removal is performed with a certain time $\Delta T$ (within the time PRR does not change), and with a certain water removal speed (water removal speed A), and thus $\Delta BV_A$, which is the volume change of the blood volume (BV) is calculated. Then, the water removal is performed for the same time as said certain time $\Delta T$ with a different water removal speed (water removal speed B), and thus, $\Delta BV_B$ which is the volume change of said BV level, is calculated. Thus, $BV_0$ can be calculated by using said $\Delta BV_A$, said $\Delta BV_B$, water removal speed A and water removal speed B, according to the following formula (II).

$BV_0$=(water removal speed A−water removal speed B)/(−$\Delta BV_A$%+$\Delta BV_B$%)×$\Delta T$     (II)

Said formula (II) can be calculated as follows.

$\Delta BV/\Delta T = PRR - UFR$ $-\Delta BV_A/\Delta T + \Delta BV_B/\Delta T$=water removal speed A−water removal speed B $BV_A = \Delta BV_0 \cdot \% \Delta BV_A$ $\Delta BV_B = \Delta BV_0 \cdot \% \Delta BV_B$ $BV_0/\Delta T(-\% \Delta BV_A + \% \Delta BV_B)$=water removal speed A−water removal speed B $BV_0/\Delta T$=(water removal speed A−water removal speed B)/(−% $\Delta BV_A$+% $\Delta BV_B$)

In the meantime, the calculating method of said primary blood volume ($BV_0$) of the present invention is, as it is clear from its calculating method, widely acceptable as long as it is a hemodialysis apparatus that carries out hemodialysis treatment by controlling the dialysis condition according to said blood indication level, being the blood volume or its changing parameter.

As for the hemodialysis apparatus of the present invention, it is possible to carry out control with the use of blood indication level, wherein the target BV % is calculated automatically according to the following formula with the use of the primary blood volume ($BV_0$) of each patient calculated as mentioned above, and the standard blood volume (BV st) which is defined beforehand by doctors and the like.

Target $BV$ %=standard blood volume($BV$ st)/primary blood volume($BV_0$)×100

Meanwhile, said standard blood volume (BV st) is a level of the blood volume (BV st) which the patient would have if healthy, defined beforehand by doctors and the like by considering factors that might influence the human blood volume, for example the patient's age, sex, body height and the like.

Definition of the blood indication level being the blood volume or its changing parameter and its calculating formula used in the hemodialysis apparatus of the present invention (1) BV volume (BV)

BV is the abbreviation of Blood Volume level and is the circulating blood volume index which is the indication level to check the condition of the circulating blood volume of each patient.

(2) $\Delta BV$ level

It is the BV volume change, and it is calculated by the following formula.

$\Delta BV$=(Ht at the time of the initiation of hemodialysis/Ht at the time of measurement)−1

Said Ht is the abbreviation of Hematocrit showing the bulk ratio of red corpuscle in the whole blood.

(3) % $\Delta BV$

It is the ratio of the blood volume change, and as shown in the following formula, the $\Delta BV$ level at the time of measurement is divided by $BV_0$ which is the BV level at the time of the initiation of dialysis and is expressed in percentage.

$\Delta BV$ %=$\Delta BV/BV_0$×100

(4) BV %

It is calculated by dividing the BV level at the time of measurement by $BV_0$ at the time of the initiation of hemodialysis and is expressed in percentage.

$$BV\% = BV \text{ level at the time of measurement}/BV_0 \times 100$$

3. Definition of other parameters of blood and their calculating formula (1) Definition of PRR PRR is an abbreviation for Plasma Refilling Rate, and is defined as speed of the blood plasma refilling from the body to the blood vessel, and shows the patient's water removal ability at each point.

(2) Formula for calculating PRR

PPR is calculated with the following formula:

$$PRR_n - UFR_n = \Delta BV_n / T_n$$

[wherein $PRR_n$ is the Plasma Refilling Rate at an optional selected measurement time point (n) of the hemodialysis, $UFR_n$ is the water removal speed at the optional selected measurement time point (n), $\Delta BV_n$ is the blood volume change at the measurement time point (n), $T_n$ is the elapsed time until the measurement time point (n), and UFR is the water removal speed, respectively.]

The hemodialysis apparatus of the present invention can perform the hemodialysis operation with water removal by determining the blood volume or the blood index level being its changing parameter, at plural time points of the chronological course of the hemodialysis operation, and by using the control line (target control line) constituted with the determined blood index level.

The control of the water removal speed in the former part of the dialysis operation of the hemodialysis apparatus with the use of said target control line is performed by using the blood indication level measured at each measurement point; and the target blood indication level showed by said target control line at the next measurement point of each measurement point.

The control of the water removal speed in the former part of the dialysis operation of the hemodialysis apparatus with the use of said target control line can be calculated according to each blood indication level of two adjacent measurement points; the water removal speed used between the two measurement points mentioned above; the blood indication level at the time of the initiation of the hemodialysis; and the target blood indication level determined by said target control line at the next measurement point of the two measurement points mentioned above.

Concretely, said control can be carried out by using the following formula (n).

$$BV_0\{-(\%\ \Delta BV_{n-1'} - \%\ \Delta BV_{n'}) + (\%\ \Delta BV_{n'} - \%\ \Delta BV_{n+1'})\} + UFR_n \times T = UFR_{n+1} \times T \quad (n)$$

(wherein $BV_0$ is the primary blood volume; $\%\ \Delta BV_{n'}$ is the ratio of the blood volume change at an optional selected measurement time point (n); $\%\ \Delta BV_{n-1'}$ is the ratio of the blood volume change at the previous measurement time point (n−1) of the selected measurement time point (n) in the former part of the dialysis operation; $\%\ \Delta BV_{n+1'}$ is the ratio of the blood volume change determined by said target control line at a measurement time point (n+1), the next measurement time point of the measurement time point (n); T is the measurement time; $UFR_n$ is the water removal speed at the selected blood measurement time point (n) in the former part of the dialysis operation; and $UFR_{n+1}$ is the water removal speed defined when the control toward the working unit is carried out, to attain the target blood indication level at a measurement time point (n+1), the next measurement point of the measurement time point (n), respectively.)

Said formula (n) is calculated as follows:

When the BV level at the time of the initiation of hemodialysis is set as $BV_0$ (primary blood volume), at each measurement point in the former part of the hemodialysis operation, for example, relational formulae as follows are obtained between BV level, PPR and UFR at the first and second measurement point.

1st Measurement Point $$BV_0\{(100\% - \%\ \Delta BV_1) - (100\% - \%\ \Delta BV_2)\} = PRR_1 - UFR_1$$

$$BV_0(-\%\ \Delta BV_{1'} + \%\ \Delta BV_{2'})/T = PRR_1 - UFR_1 \quad (1)$$

2nd Measurement Point $$BV_0(-\%\ \Delta BV_{2'} + \%\ \Delta BV_{3'})/T = PRR_2 - UFR_2 \quad (2)$$

Here, $BV_0$, $\%\ \Delta BV_{1'}$, $\%\ \Delta BV_{2'}$, and T show the BV level at the time of the initiation of hemodialysis, the ratio of the BV volume change at the first or second measurement point and the elapsed time of dialysis, respectively. Moreover, $\%\ \Delta BV_3$ is determined by the target control line.

Similar relations are also obtained at each optional measurement points, (n−1) or (n), as it is shown in the following relational formulae.

(n−1)th measurement point $$BV_0(-\%\ \Delta BV_{n-1'} + \%\ \Delta BV_{n'})/T = PRR_{n-1} - UFR_{n-1}$$

(n)th measurement point $$BV_0(-\%\ \Delta BV_{n'} + \%\ \Delta BV_{n+1'})/T = PRR_n - UFR_n$$

By subtracting said formula (2) from said formula (1), the following formula (3) is obtained.

$$BV_0\{(\%\ \Delta BV_{1'} - \%\ \Delta BV_{2'}) - (\%\ \Delta BV_{2'} - \%\ \Delta BV_3)\}/T = PRR_1 - PRR_2 + UFR_2 - UFR_1 \quad (3)$$

When it is hypothecated there is no difference between $PRR_1$ and $PRR_2$, that is the distance between the measurement points are defined to be short so as the patient's PPR is not changed substantively at each measurement point, the first and second terms in the right side are deleted. Thus, the following formula (4) is obtained.

$$BV_0\{-(\%\ \Delta BV_{1'} - \%\ \Delta BV_{2'}) + (\%\ \Delta BV_{2'} - \%\ \Delta BV_3)\}/T + UFR_1 = UFR_2 \quad (4)$$

In this formula, $\%\ \Delta BV_3$ is the target level at the next measurement point, and is a level for the blood indication level to approach by carrying out the control. Furthermore, $UFR_2$ is the water removal speed to define so that the blood indication level at the next measurement point approaches the target level mentioned above. Here, $BV_0$, $\%\ \Delta BV_{1'}$, $\%\ \Delta BV_{2'}$, T are well known as the BV level at the time of the initiation of dialysis, the ratio of the blood volume change at the first or second measurement point, and the elapsed time of dialysis, respectively. Moreover, $UFR_1$ is also well known as the water removal speed from the first measurement point to the second measurement point. Therefore, if $\%\ \Delta BV_3$, which is the target ratio of the BV volume change is specified, the water removal speed being a dialysis condition can be calculated with the formula (4). The target BV level can be determined by the target control line, from the measurement point. On the contrary, if the hemodialysis treatment is carried out with that water removal speed, the BV level at the next measurement point can approach the target level, that is the target control line.

When describing the above formula for an optional measurement point (n), of hemodialysis, it is shown as the following formula (n), and as described above, the water removal speed to be defined so that the blood indication level approaches the target at the next point is determined by the BV volume change at the two measurement points; the water removal speed between the two measurement points; the measurement level of the dialysis time T; and the blood indication level defined at the next measurement point of the two measurement points mentioned above, determined according to the target control line of said blood indication level.

$$BV_0\{-(\%\ \Delta BV_{n-1'}-\%\ \Delta BV_{n'})+(\%\ \Delta BV_{n'}-\%\ \Delta BV_{n+1})\}/T+UFR_n=UFR_{n+1} \quad (n)$$

In said formula, $BV_0$ is the primary blood volume % $\Delta BV_{n'}$ is the ratio of the blood volume change at an optional selected measurement time point (n) in the former part of the dialysis; % $\Delta BV_{n-1'}$ is the ratio of the blood volume change at the previous measurement point of the measurement time point (n) % $\Delta BV_{n+1}$ is the ratio of the blood volume change defined at a measurement time point to carry out feed-forward control; T is the measurement time; $UFR_n$ is the water removal speed at the selected measurement point in the former part of the dialysis operation; and $UFR_{n+1}$ is the water removal speed defined at the next measurement point from the selected measurement point (n) in the former part of the dialysis operation, when the control is carried out toward the working unit, to attain the target blood indication level, respectively. However, to obtain said formulae (4) and (n), the condition that "there is no difference between the PRRs at each measurement point", which was hypothecated to derive these formulae, is an assumption, and to meet this condition, it is important that the distance between each measurement point ($\Delta T$) is defined to be short so that there is no difference between the PRRs. Moreover, as for this controlling method, errors to the control may occur due to errors of $BV_0$ at the time of the initiation of dialysis, control delay and other factors, but in the actual control, the control is ensured by defining the water removal speed at each point (measurement point).

In other words, as for the water removal operation in the former part of the dialysis operation mentioned above, as it is described above, the distance between each measurement point is defined to be short and the water removal speed is defined each time, the errors occurring substantively cause no problems.

The water removal is performed by controlling the water removal speed with a controlling means as mentioned above, and when the blood volume circulating in the body approaches the standard blood volume, the dialysis operation of the latter part of the hemodialysis operation is started. When the hemodialysis operation of the latter part of the dialysis operation is started, the remaining water removal volume of the target water removal volume is measured or calculated, and the water removal speed is calculated again to finish removing said water removal volume within the target water removal time, and the water removal of the latter part of the hemodialysis operation can be performed with said water removal speed.

As for the water removal operation of the hemodialysis apparatus of the present invention, it is preferable to determine beforehand the maximum water removal speed separately for the former part of the hemodialysis operation and the latter part of the hemodialysis operation, respectively, and when the water removal speed calculated in the former part or latter part of the hemodialysis operation mentioned above, exceeds said maximum water removal speed, to control so that the water removal is performed with said maximum water removal speed.

As for the control of the water removal operation of the hemodialysis apparatus of the present invention, it is preferable to define separately for the former part and the latter part of the dialysis operation, respectively, a deviated control line (alarm line) to limit the chronological change of the blood indication level within a predetermined range, under said target control line, and when said blood indication level exceed said deviated control line (alarm line), to carry out by controlling the working means that carries out the hemodialysis treatment so that the dialysis condition to recover said blood indication level to be above said deviated control line (alarm line) is performed.

As for means to recover said blood indication level to be above said deviated control line (alarm line), there is means to stop temporarily the water removal means.

In the former part of the dialysis operation, when the means to recover the blood indication level to be above said deviated control line (alarm line) is performed, and at the time the blood indication level is recovered to be above said deviated control line (alarm line) as a result, the dialysis operation is started again according to the control of the former part of the hemodialysis operation. Furthermore, in the latter part of the hemodialysis operation, when the means to recover the blood indication level to be above said deviated control line (alarm line) is performed, and at the time the blood indication level is recovered to be above said deviated control line (alarm line) as a result, the water removal speed is calculated again so that the remaining water removal volume at that time is finished to be removed within the target water removal time, and the hemodialysis operation of the latter part of the dialysis operation of the latter part of the dialysis operation is started again with said water removal speed.

Furthermore, as for the control of the water removal operation for the hemodialysis apparatus of the present invention, especially in the latter part of the hemodialysis operation, it is preferable to enable to control so that the blood indication level is recovered rapidly to be above said deviated control line (alarm line), and in case the blood indication level reaches downward by further exceeding said urgent substitutive fluid supply line, not only to stop temporarily the working means that carries out blood treatment as mentioned above, but to use also a substitutive fluid supply means to inject substitutive fluid into the body.

Furthermore, the present inventors have found that as for the control of the water removal speed with the use of said target control line, the change of the blood volume appears after the change of the water removal speed (especially at the point when the target control line drastically changes). Moreover, they have found that when the feed forward control mentioned above is carried out by ignoring said phenomenon, there is a problem that the control is not stable, and they have proposed to solve the problems occurred form said control delay by considering said control delay (Japanese patent application 2002-19447), to solve this object. However, as for means proposed above, for example means for calculating the forecast of the dialysis condition necessary to attain the next target blood indication level (blood volume change) according to the blood indication level at the point the control delay time has passed, in the controlling method of the water removal speed using said target control line, can be used when a problem of control delay as mentioned above occurs in the controlling method of the water removal speed which uses said target control line of the present invention.

In the following, parameters concerning blood and blood indication level and blood used in the hemodialysis apparatus of the present invention, will be explained concretely.

1. Primary Blood Volume ($BV_0$)

It is preferable to use the patient's inherent primary blood volume as one of the controlling factors in the former part of the dialysis operation. Said patient's inherent primary blood volume can be calculated for example by the two following methods.

(1) The First Method for Calculating the Primary Blood Volume ($BV_0$)

The first method for calculating the primary blood volume ($BV_0$) is explained according to FIG. 3.

At the time of the initiation of dialysis, as the blood volume is not stable, the water removal is not performed, and only circulation outside the body is performed. By continuing circulation outside the body until the blood volume stabilizes, in case the turgor pressure inside the cells is sufficiently high, and the water runs over the cells and is accumulated up to the cell stroma, it is believed that the body fluid (the inflow volume from the cells of FIG. 3) corresponding to the increased blood volume circulating outside the body (space outside the body) will move from the cells to the blood vessel. Therefore, it is possible to obtain the primary blood volume ($BV_0$) of each patient, according to the following formula (I) with the increased blood volume circulating outside the body (space outside the body) and $\% \Delta BV_x$.

$$\text{Primary blood volume}(BV_0) = \text{increased blood volume circulating outside the body(space outside the body)}/\% \Delta BV_x \qquad (I)$$

($\% \Delta BV_x$ is the ratio of the blood volume change when only circulation outside the body is performed without performing water removal.)

(2) The Second Method for Calculating the Primary Blood Volume ($BV_0$)

The primary blood volume ($BV_0$) of each patient can be obtained also by the following method. Said second calculating method is explained according to FIG. 4.

By using the hemodialysis apparatus which controls dialysis conditions according to the blood indication level, only circulation outside the body is performed without performing water removal, at the time of the initiation of dialysis as shown in FIG. 4, said circulation outside the body is continued until the blood volume (BV) level stabilizes, and when the blood volume (BV) level becomes stable, dialysis accompanied by water removal is initiated, and at the same time as said dialysis is initiated, the water removal is performed with a certain time $\Delta T$ (within the time PRR does not change), and with a certain water removal speed (water removal speed A), and thus $\Delta BV_A$, which is the volume change of said BV level is calculated. Then, the water removal is performed for the same time as said certain time $\Delta T$ with a different water removal speed (water removal speed B), and thus, $\Delta BV_B$ which is the volume change of said BV level, is calculated. Thus, $BV_0$ can be calculated by using said $\Delta BV_A$, said $\Delta BV_B$, water removal speed A and water removal speed B.

The primary blood volume ($BV_0$) of each patient calculated by said second method, can be calculated concretely according to the following formula (II).

$$BV_0 = (\text{water removal speed } A - \text{water removal speed } B)/(-\Delta BV_A \% + \Delta BV_B \%) \times \Delta T \qquad (II)$$

Said formula can be calculated as follows. The calculating method is explained according to FIG. 4.

$$\Delta BV/\Delta T = PRR - UFR$$

$$-\Delta BV_A/\Delta T + \Delta BV_B/\Delta T = \text{water removal speed } A - \text{water removal speed } B$$

$$\Delta BV_A = \Delta BV_0 \cdot \% \Delta BV_A$$

$$\Delta BV_B = \Delta BV_0 \cdot \% \Delta BV_B$$

$$BV_0/\Delta T(-\% \Delta BV_A + \% \Delta BV_B) = \text{water removal speed } A - \text{water removal speed } B$$

$$BV_0/\Delta T = (\text{water removal speed } A - \text{water removal speed } B)/(-\% \Delta BV_A + \% \Delta BV_B)$$

As for the hemodialysis apparatus of the present invention, it is preferable that it is a constitution that enables to carry out control with the use of blood indication level, wherein the target BV % is calculated automatically according to the following formula with the use of the primary blood volume ($BV_0$) of each patient calculated as mentioned above, and the standard blood volume (BV st) which is defined beforehand by doctors and the like.

$$\text{Target } BV \% = \text{standard blood volume}(BV\ st)/\text{primary blood volume}(BV_0) \times 100$$

Meanwhile, said standard blood volume (BV st) is a level of the blood volume (BV st) which the patient would have if healthy, defined beforehand by doctors and the like by considering factors that might influence the human blood volume, for example the patient's age, sex, body height and the like.

In the meantime, the calculating method of said primary blood volume ($BV_0$) of the present invention is, as it is clear from its calculating method, it is not limited to the hemodialysis apparatus controlling the water removal operation by dividing the dialysis operation to the former and latter part, and it is widely acceptable as long as it is a hemodialysis apparatus that carries out hemodialysis treatment by measuring or calculating the blood volume or its volume change as the blood indication level to control the dialysis condition according to said blood indication level.

2. Definition of the Blood Indication Level being the Blood Volume or its Volume Change and its Calculating Formula (1) BV Level BV level is the abbreviation of Blood Volume level and is the circulating blood volume index which is the indication level to check the condition of the circulating blood volume of each patient.

(2) $\Delta BV$ Level

It is the BV volume change, and it is calculated by the following formula.

$$\Delta BV[BV \text{ volume change}] = (Ht \text{ at the time of the initiation of dialysis}/Ht \text{ at the time of measurement}) - 1$$

Said Ht is the abbreviation of Hematocrit showing the bulk ratio of red corpuscle in the whole blood.

(3) % ΔBV

It is the ratio of the blood volume change, and as shown in the following formula, the ΔBV level at the time of measurement is divided by $BV_0$ which is the BV level at the time of the initiation of dialysis and is expressed in percentage.

$$\Delta BV\% = \Delta BV/BV_0 \times 100$$

(4) BV %

It is calculated by dividing the BV level at the time of measurement by $BV_0$ at the time of the initiation of dialysis and is expressed in percentage.

$$BV\% = BV \text{ level at the time of measurement}/BV_0 \times 100$$

3. Definition of other Parameters of Blood and their Calculating Formula (1) Definition of PRR PRR is an abbreviation for Plasma Refilling Rate, and is defined as speed of the blood plasma refilling from the body to the blood vessel, and shows the patient's water removal ability at each point.

(2) Formula for calculating PRR

PPR is calculated with the following formula:

$$PRR_n - UFR_n = \Delta BV_n/T_n$$

[wherein $PRR_n$ is the Plasma Refilling Rate at an optional selected measurement point (n), $UFR_n$ is the water removal speed at an optional selected measurement point (n), $\Delta BV_n$ is the blood volume change at an optional selected measurement point' (n), $T_n$ is the elapsed time until an optional selected measurement point (n), and UFR is the water removal speed, respectively.]

Hereinafter, the target control line, the data line and the estimated control line used in the hemodialysis apparatus of the present invention will be explained.

Figure 2:
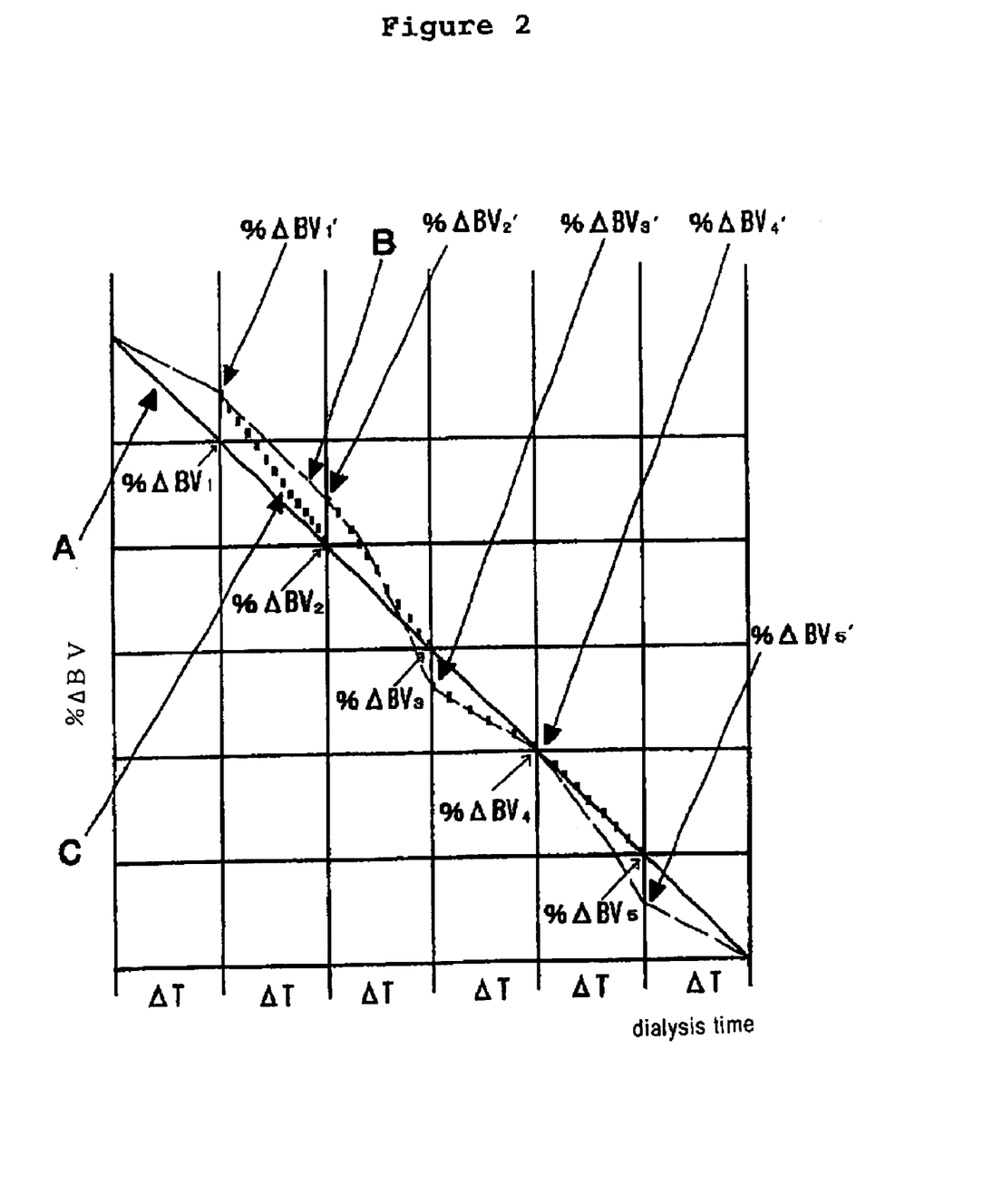
FIG. 2 is a figure showing the control in the former part of the water removal operation of the blood treatment apparatus.

The longitudinal axis of FIG. 2 is % ΔBV level, and the horizontal axis shows the elapsed time form the initiation of dialysis.

Figure 1:
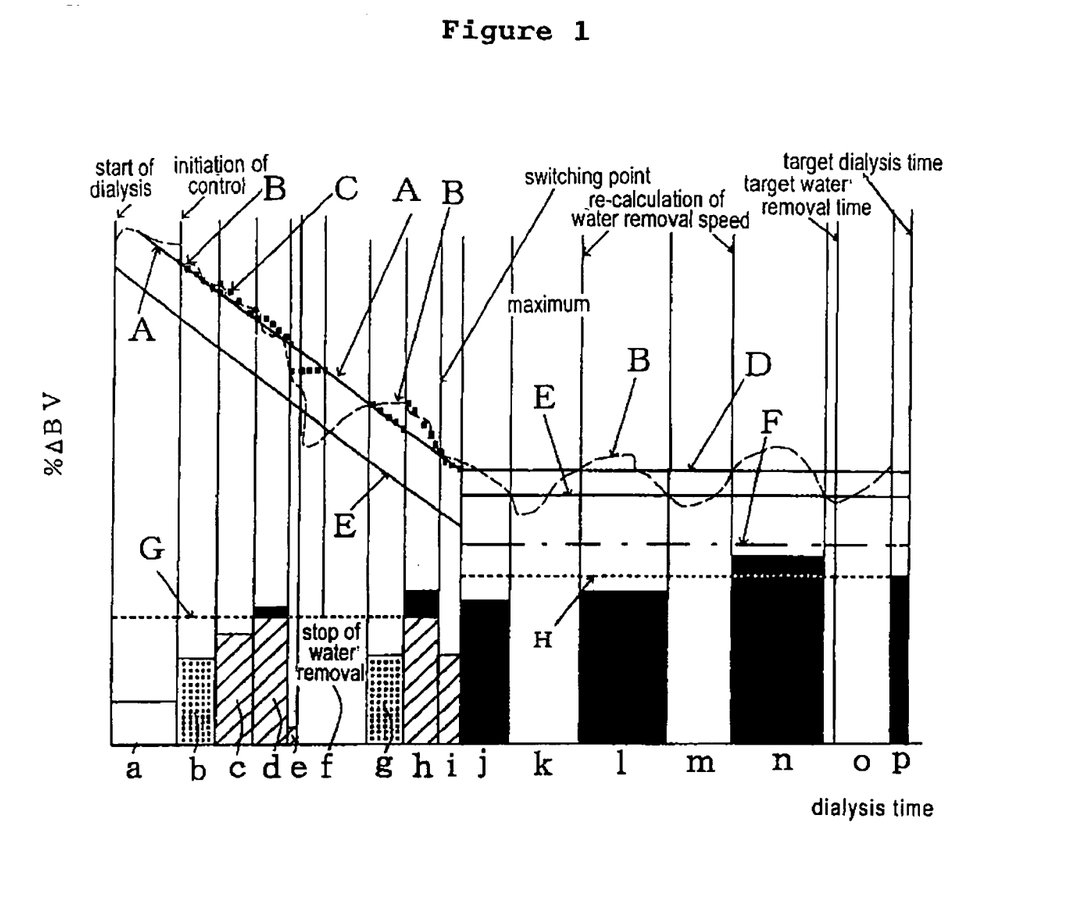
FIG. 1 is a figure explaining the controlling method of the entire water removal operation of the blood treatment apparatus.

(1) Target Control Line:

It is shown by a hatched line A in the former part of the dialysis in FIG. 1 and in FIG. 2, and by a horizontal line D in the latter part of dialysis. According to this target control line of FIG. 1, in the former part of the dialysis operation, a hemodialysis operation, for example water removal, which decreases the blood volume reasonably to the body is performed, and in the latter part of dialysis operation, a dialysis operation, for example water removal, which maintains the blood volume suitable to each patient according to the target control line, that is, to maintain the standard blood volume substantively constant is performed. Therefore, this target control line is an indication of the chronological course or the chronological target level of the blood indication level. In the meantime, said target control line is defined before hemodialysis by doctors and the like, and its angle of gradient is determined by the relation with the target water removal volume.

(2) Data Line and Estimated Control Line

It will be explained according to FIGS. 1 and 2. The data line B is the ratio of the blood volume change composed with data level of the blood indication level of % $\Delta BV_1$, $\Delta BV_2$, and the like. The estimated control line near by the target control line A is determined as follows: by using the blood indication level according to the measurement levels such as BV, ΔBV or % ΔBV and the like at the measurement point (controlling point); and the target blood indication level shown by said target control line A at the next measurement point (controlling point), the dialysis conditions (for example, the water removal speed) to attain the target blood indication level at the next measurement point (controlling point) is calculated, and the hemodialysis treatment is carried out under this calculated dialysis conditions (for example, the water removal speed), to attain the next measurement point (controlling point). As a result, the data line B which will likely slip away from the target control line A, will be corrected by the dialysis conditions newly defined at every measurement point (controlling point), and therefore become the estimated control line C, which transits along said target control line A.

(3) Deviated Control Line (Alarm Line) and Urgent Liquid Supply Line

The hatched line downward sloping shown beneath the target control line in the former part of the dialysis operation, and the horizontal line in the latter part of the dialysis operation in FIG. 1, is the deviated control line (alarm line) E to function as a deviated control line (alarm line). Furthermore, the horizontal line defined under the deviated control line (alarm line) E in the latter part of the dialysis operation is the urgent liquid supply line F.

In case hemodialysis operation is carried out under the control of the hemodialysis apparatus of the present invention, in case the blood indication level actually measured in the former and latter part of the dialysis operation exceeds said deviated control line (alarm line) E, it is preferable to adapt an emergency control, and for example in the former part of the dialysis operation, it is preferable to adapt an emergency control different from the feed-forward control which uses said target control line. For example, as it is shown in the graph in FIG. 1, in case the data line showing the transition of the data level deviates beneath the alarm line E, the water removal means such as water removal pump and the like should be stopped, or in case the data line deviates beneath the urgent substitutive fluid supply line F, if necessary, a substitutive fluid replacement to the patient using a fluid replacement pump is performed by priority before carrying out the control by feed-forward.

As mentioned above, the hemodialysis apparatus of the present aspect does not only have the function to approach the blood indication level to the target, but in case (the blood indication level is) deviated in a dangerous region, it is possible to ensure the safety of the patient by preferentially operating the emergency control. Moreover, the defined water removal speed is shown in the bottom half of the graph in FIG. 1.

The hemodialysis apparatus of the present invention stops the water removal means such as water removal pump and the like by using said deviated control line (alarm line) E or urgent substitutive fluid supply line F, or if necessary performs a substitutive fluid replacement to the patient using a substitutive fluid replacement pump by priority, also in the latter part of hemodialysis operation, as described above. Therefore, the hemodialysis apparatus of the present invention does not only have the function to approach easily the primary blood volume (BV0) the standard blood volume in the former part of the dialysis operation, but in the former part of the dialysis operation and/or in the latter part of the dialysis operation, in case (the blood indication level is) deviated in a dangerous region, it is possible to ensure the safety of the patient by preferentially operating the emergency control.

In the latter part of the dialysis operation, at the time that the water removal volume that was planned to be removed in the former part of the dialysis operation was removed, the water removal control of the latter part of the dialysis operation is started. At this time, the water removal speed is calculated to finish removing the remaining water removal volume within the target water removal time, and the water removal is performed with said water removal speed. However, in case said water removal speed exceed the maximum water removal speed line defined for the latter part of the dialysis operation, the hemodialysis is carried out with the maximum water removal speed, as for the former part of the dialysis operation.

INDUSTRIAL APPLICABILITY

By using the hemodialysis apparatus of the present invention, excellent effects such as (1)–(3), as follows, can be obtained.
(1) The control mechanism is simple, and there is little risk of misoperation or out-of-control.
(2) As there is no need of difficult installation or unnecessary operation, the operator can easily operate without difficulty.
(3) As the control is carried out rapidly and finely, the blood volume can be transited fairly during the hemodialysis.

BRIEF DESCRIPTION OF DRAWINGS

In FIG. 1, (a) is the period performing only circulation outside the body without performing water removal, (b) is the water removal period at the time of the initiation of the water removal, (c), (d), (e), (f), (g), (h), (i), (j), (k), (l), (m), (n), (o) and (p) are water removal speed determined with the use of said target control line, alarm line E and maximum water removal line G or H, used in the corresponding period. In FIG. 2, % $\Delta BV_{1'}$, % $\Delta BV_{2'}$, % $\Delta BV_{3'}$, % $\Delta BV_{4'}$, and % $\Delta BV_{5'}$ are the ratio of the blood volume change measured at the measurement point 1, 2, 3, 4 and 5; % $\Delta BV_1$, % $\Delta BV_2$, % $\Delta BV_3$, % $\Delta BV_4$, and % $\Delta BV_5$ are the ratio of the blood volume change determined by the target control line at the measurement point 1, 2, 3, 4 and 5. Further, $\Delta T$ is the interval of measurement time between each measurement point. Moreover, A is the control line (former part), B is the data line, C is the estimated control line, D is the control line (latter part), E is the deviated control line (alarm line), F is the urgent liquid supply line, G is the maximum water removal speed line, and H is the maximum water removal speed line, respectively.

BEST MODE OF CARRYING OUT THE INVENTION

1. EXAMPLE 1

The embodiments of control for hemodialysis operation of the hemodialysis apparatus of the present invention is explained according to FIG. 1. In the bottom half of FIG. 1, the defined water removal speed is shown.

As it is shown in FIG. 1, the maximum water removal speed line G and H are defined in the former and latter part of the dialysis operation, in the bottom half of FIG. 1, the defined water removal speed (or the history) in the former and latter part of the dialysis operation are shown.

Former Part of the Dialysis Operation (1) Start of Dialysis

When starting dialysis, as the BV level is unstable, the water removal is not performed at the time of the initiation of dialysis (water removal speed is 0), only circulation outside the body is performed, and it is waited for the time interval to pass until the BV level stabilizes (period a). During the period a, the patient's primary blood level ($BV_0$) could be calculated according to the above (I).

(2) The Time of the Initiation of the Water Removal

After the BV value stabilizes, the hemodialysis apparatus is reset and the measurement is started again. At this time, the patient's primary blood level ($BV_0$) can be calculated according to the above (II), instead of calculating the patient's primary blood level $BV_0$) according to the above (I). The hemodialysis operation after the BV level is stabilized, the control of the water removal means by feed-forward control according to the above formula (n) of said target control line A was performed. Among the water removal speed (c)–(i) in the former part of the hemodialysis operation determined with the control method mentioned above, the water removal speed d and h in the former part of the hemodialysis operation exceed the maximum water removal speed line G, therefore the maximum water removal speed is adapted. In the meantime, when the water removal speed exceeds the maximum water removal speed line, it is most preferable to adapt the maximum water removal speed as said water removal speed, but it may be a water removal speed less than the maximum water removal speed. Moreover, as the data level of the blood volume or the blood volume change during dialysis at water removal speed (f), becomes less than that of the alarm line, the water removal speed is set f=0 (that is, water removal is not performed).

(3) Restart of the Water Removal

In the former part of the dialysis operation, when the blood volume or the blood volume change becomes less than the alarm level, the water removal is stopped (water removal speed f=0), but when the blood volume or the blood volume change exceeds the control line as a result of the termination of water removal, the water removal is started again. As for the primary water removal speed of the control at the time of starting again, the water removal is performed with the water removal speed predicated by the method mentioned above. At the time when the water removal volume predicted to be removed in the former part of the hemodialysis operation is removed and the standard blood volume approaches, or at the time when the ratio of the blood volume (% BV) becomes the object blood volume ratio (object % BV), the control of water removal of the latter part of hemodialysis operation is started.

Latter part of hemodialysis operation

The water removal speed is calculated to finish removing the remaining water removal volume within the target water removal time, and the water removal is performed with said water removal speed. When performing water removal with this water removal speed, the water removal is stopped in case the blood volume or the blood volume change becomes less than said alarm level. When the blood indication level attains downward by exceeding the urgent liquid supply line defined beneath said deviated control line (alarm line), not only the working means that carries out blood treatment as mentioned above is stopped temporarily, but the blood indication level is recovered rapidly to be above said deviated control line (alarm line) by using the liquid supply means to inject liquid supply inside the body together. For example, when the water removal is performed with the water removal speed (j), the blood volume or the blood volume change became less than said alarm level. Therefore, the water removal at the next controlling point is stopped, and the water removal speed (k) was set to 0.

Moreover, as a result of termination of said water removal, the actual blood volume change $\Delta BV$ level have been recovered to be above said alarm level, the water removal speed is calculated so that the remaining water removal volume at that controlling point is finished to be removed within the target water removal time (determined water removal volume), and the water removal is performed with said determined water removal speed (1). By performing the water removal with said determined water removal speed (1), the actual $\Delta BV$ level becomes less than said alarm level again. Therefore, the water removal at the next controlling point is stopped and the water removal speed (in) was set to 0. Furthermore, as a result of termination of said water removal, the actual $\Delta BV$ level have been recovered to be above the control line, the water removal speed is calculated so that the remaining water removal volume at that controlling point is finished to be removed within the target water removal time (determined water removal volume), and the water removal is performed with said determined water removal speed (n). However, as said determined water removal speed (n) exceeds the maximum water removal speed line H, the maximum water removal speed was adapted as the actual water removal speed. As the target water removal volume was not finished to be removed by the end of the target water removal time, the water removal was performed with the maximum water removal speed up to the target removal volume, and the hemodialysis was finished.

The invention claimed is:

1. A hemodialysis apparatus, comprising:
   means for measuring or calculating a blood volume or a blood volume change as a blood index level;
   a hemodialysis means; and
   a controlling means for controlling hemodialysis conditions of the hemodialysis means according to the blood index level,
   wherein the controlling means controls the hemodialysis means so that a hemodialysis operation is carried out without performing water removal when initiating the hemodialysis operation until the blood volume stabilizes, and the hemodialysis operation is carried out by performing water removal after the blood volume is stabilized by the hemodialysis operation, and
   wherein the controlling means enables calculation of a primary blood volume ($BV_0$) of an individual according the equation:

$(BV_0)$=increased blood volume circulating outside the body (space outside the body)/% $\Delta BV_x$, wherein % $\Delta BV_x$ is a ratio of the volume change of the blood volume (BV) when the hemodialysis operation is performed without performing water removal.

2. A hemodialysis apparatus, comprising:
   means for measuring or calculating a blood volume or a blood volume change as a blood index level;
   a hemodialysis means; and
   a controlling means for controlling hemodialysis conditions of the hemodialysis means according to the blood index level,
   wherein the controlling means controls the hemodialysis means so that a hemodialysis operation is carried out without performing water removal when initiating the hemodialysis operation until the blood volume stabilizes, and the hemodialysis operation is carried out by performing water removal after the blood volume is stabilized by the hemodialysis operation,
   wherein the controlling means controls the hemodialysis means so that water removal is performed with a water removal speed A within $\Delta T$ (a time that a plasma refilling rate (PRR) does not change) when initiating the hemodialysis operation with water removal, and then to perform subsequently water removal with a water removal speed B which is different from the water removal speed A, within $\Delta T$, and
   wherein the controlling means enables calculating the primary blood volume ($BV_0$) according to the equation:

$BV_0$=(water removal speed $A$–water removal speed $B$)/(–% $\Delta BV_A$ % $\Delta BV_B$)×$\Delta T$, wherein % $\Delta BV_A$ is a ratio of the volume change of the blood volume (BV) when the water removal is performed with the water removal speed A and % $\Delta BV_B$ is a ratio of the volume change of the blood volume (BV) when the water removal is performed with the water removal speed B.

* * * * *